United States Patent [19]
Jacobs et al.

[11] Patent Number: 5,434,249
[45] Date of Patent: Jul. 18, 1995

[54] METHOD FOR MODULATING SPECIFIC ACTIVITY OF INTEFERON ALPHA

[75] Inventors: Dana B. Jacobs, Cooper City, Fla.; David C. Munch, Montville, N.J.

[73] Assignee: Viragen Inc., Fla.

[21] Appl. No.: 889,136

[22] Filed: May 27, 1992 (Under 37 CFR 1.47)

[51] Int. Cl.⁶ .............................................. C07K 17/02
[52] U.S. Cl. .................................... 530/351; 530/413; 530/362; 530/363; 530/354
[58] Field of Search .............. 530/351, 413, 362, 363, 530/354; 424/85.4, 85.7

[56] References Cited

U.S. PATENT DOCUMENTS

| | | | |
|---|---|---|---|
| 4,172,071 | 10/1979 | De Maeyer et al. | 424/85.4 |
| 4,289,690 | 9/1981 | Pestka et al. | 530/413 |
| 4,489,166 | 12/1984 | Joshi | 436/510 |
| 4,503,035 | 3/1985 | Pestka et al. | 530/351 |
| 4,617,378 | 10/1986 | Rubinstein et al. | 530/351 |
| 4,686,284 | 8/1987 | Nara et al. | 530/351 |
| 4,847,079 | 7/1989 | Kwan | 424/85.4 |

Primary Examiner—Michael G. Wityshyn
Assistant Examiner—C. Sayala
Attorney, Agent, or Firm—Cowan, Liebowitz & Latman

[57] ABSTRACT

A method for modulating the specific activitiy of a target protein which is being purified. A controller protein is added to the target protein prior to conducting a final purification step in a purification process.

3 Claims, 1 Drawing Sheet

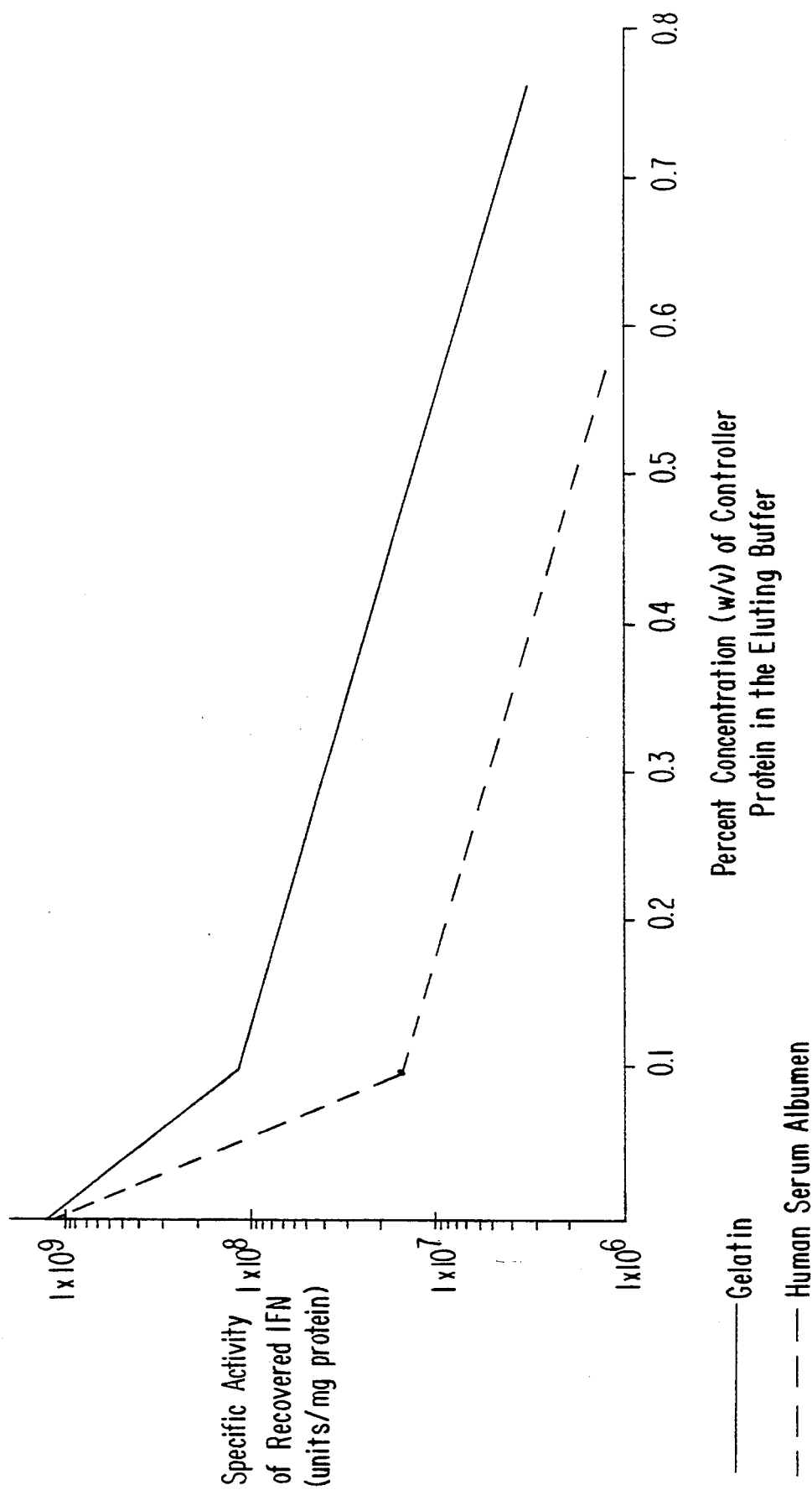

METHOD FOR MODULATING SPECIFIC ACTIVITY OF INTEFERON ALPHA

BACKGROUND OF THE INVENTION

1. Field of the Invention

This invention relates to a method for modulating the specific activity of a purified protein product while purifying the protein. More particularly, the specific activity of a purified protein is modulated by addition of a controller protein at one or more points during the course of a purification protocol.

2. Description of Related Art

Interferon is a protein which is produced by a host organism upon infection by viruses, or by an immunoreaction such as an antigen-antibody reaction. Interferon has an antiviral affect.

There are several known processes used to produce interferon. Leukocytes or lymphoblastoid cells can be stimulated to produce interferon with appropriate viruses or lectins. Fibroblast cells may also be stimulated to produce interferon with viruses or a synthetic nucleic acid. Recent developments in recombinant DNA technology make it possible to produce interferon from cellular culture, i.e., from either mammalian cells or micro-organisms such as bacteria or yeast which are transformed with a plasmid carrying an interferon gene.

Interferon is classified into three categories according to its origins. Leukocytes and lymphoblastoid cells stimulated with viruses produce interferon-alpha, those cells stimulated with lectins produce interferon-gamma and fibroblast cells stimulated with a synthetic nucleic acid produce interferon-beta.

When interferon is harvested from cell culture, it normally is found in a crude supernatant liquid which must be further purified in order to obtain a product which is suitable for clinical use. Numerous processes or protocols have been developed to effect such purification. These processes usually involve several complex steps wherein the final interferon yield may be anywhere between 10% to 70% of the starting material. The majority of human interferon used today is produced and purified essentially according to the procedure developed by Kari Cantell et al. as described in "Partial Purification of Human Leukocyte Interferon On a Large Scale" appearing in Methods in Enzymology, Vol. 78, page 499–505, the contents of which are incorporated herein by reference. Techniques which have been employed to purify interferon include precipitation, gel filtration, ion exchange chromatography, gel electrophoresis, affinity chromatography, and high pressure liquid chromatography. These techniques take advantage of various physical and chemical properties associated with the protein.

U.S. Pat. No. 4,503,035 to Pestka, et al., describes a process for purifying proteins, particularly proteins having molecular weights in excess of 12,000 kilodaltons involving applications of high performance liquid chromatography to provide homogenous interferon having a specific activity of from $0.9 \times 10^8$ to $4 \times 10^8$ units/mg. of protein when assayed on the MDBK bovine cell line and from $2 \times 10^6$–$7.6 \times 10^8$ units/mg. of protein when assayed on the AG 1732 human cell line. Specific activity for interferons and other proteins is defined as the number of units of biological activity per milligram of protein mass. Alpha interferon preparations made according to the Cantell method normally run between $1.0$–$10.0 \times 10^6$ units per milligram of protein.

In addition to specific activity, other criteria for assessing the relative purity of a purified protein include molecular weight determination, mass spectroscopy, and sequencing. Specific activity is useful in assessing the relative purity of the protein product and is consequently useful in determining effective dosage of the protein. Thus, the ability to effectively control the specific activity of the end product of the purification process is a desirable goal.

SUMMARY OF THE INVENTION

The present invention relates to a method for controlling resulting specific activity of a target protein by adding an effective amount of a controller protein prior to the final step in the purification of the target protein. In a preferred embodiment, albumin or gelatin is added to a buffer which is used to elute interferon from a immunoaffinity column.

BRIEF DESCRIPTION OF THE DRAWING

FIG. 1 illustrates the relationship between specific activity of recovered target protein and the addition of controller protein in accordance with the present invention.

DETAILED DESCRIPTION OF THE INVENTION

In accordance with the present invention, specific activity of a target protein product can be made higher or lower depending upon the addition of a controller protein during the course of purification of the target protein. The controller protein increases the quantity of total protein in a sample and thus affects the specific activity of the samples by lowering the proportionate amount of target protein in the sample.

The specific activity of a protein normally is increased from step to step in a purification process. For example, as is described in the Peska et al. U.S. Pat. No. 4,503,035, whose contents are incorporated herein by reference, a series of ten steps are used in the purification of human leukocyte interferon from the incubation medium in which cells are grown and made to express interferon through to a final Lichrosorb RP-8 (pH 4) purification step. The relative specific activity, in units per milligram, of interferon in the incubation medium is $5 \times 10^3$ and purification results in a product which is between 60,000 to 80,000-fold purer than the incubation medium.

In accordance with the present invention, specific activity of interferon is modulated by addition of various levels of a controller protein such as human serum albumin to an eluate buffer used in immunoaffinity chromatography. Use of immunoaffinity chromatography is preferred because albumin binds to interferon and is carried through the immunoaffinity chromatography column along with the interferon and serves to both stabilize and define specific activity of the end product. In addition, the albumin is not separated from the interferon by this chromatographic method. Thus, after treatment with immunoaffinity chromatography, the final product consists of interferon, albumin and eluate buffer, the interferon having modulated specific activity.

As can be seen from FIG. 1, which can be used to compare the weight/volume percentage of human serum albumin or gelatin in the eluting buffer to specific activity of recovered interferon, increasing the amount or percentage of human serum albumin in the eluting buffer causes a corresponding decrease in the specific activity of recovered interferon. For example, elution with 0.1% w/v of human serum albumin in eluent buffer yields a specific activity of recovered interferon of approximately $6.3 \times 10^7$ units/mg., elution with 0.5% w/v of human serum albumin in eluent buffer yields a specific activity of approximately $9.4 \times 10^6$ units/mg. Elution with 0.1% w/v of gelatin in eluent buffer yields a specific activity of about $3.2 \times 10^8$ units/mg. and elution with 0.5% w/v of gelatin in eluent buffer yields a specific activity of about $5.2 \times 10^7$ units/mg.

It is contemplated that other proteins may be added to the eluent to modulate the specific activity of various target proteins. In essence, any protein which is capable of immunoaffinity purification (purification by complexation with antibodies) is an ideal candidate for modulation of specific activity by the method of the present invention. The controller protein, e.g., albumin or gelatin, may also be varied as long as the controller protein is fairly innocuous, i.e., it does not irreversibly destroy the activity of the protein. Such characteristics of proteins are well known to those with skill in the art.

The following example is illustrative of the present invention and is not intended to be a limitation thereon.

EXAMPLE

Virus induced human leukocyte alpha interferon was produced according to the methods of Cantell, supra, as described below. Crude interferon is pooled and successively precipitated in 0.5M KSCN at room temperature. pH is lowered to 3.8 and the solution is centrifuged at 1,000 g for 30 minutes. The supernatant solution of KSCN is discarded and cold ethanol is poured on the pellet which is shaken loose and transferred to a blender. The suspension is blended at 21,000 rpm for 5 seconds at 5 second intervals. The ethanol extract is then centrifuged at approximately $-5°$ at 1,600 g for 30 minutes and the precipitate is discarded. The pH of the supernatant is raised to 5.5 at between 0° and 4° centigrade. The solution is centrifuged at 1,600 g for 30 minutes and the precipitate is discarded. The pH of the supernatant is then raised to 5.75 at approximately 0° to 4° centigrade and centrifuged at 1,600 g for 30 minutes.

Although the Cantell method continues on to other steps, the pH 5.75 supernatant is then centrifuged at 12,000 RPM (approximately 14,700 g for 90 minutes). The supernatant is decanted, saved and the precipitate discarded. The sample supernatant is then dialyzed against two 10-fold changes of phosphate buffer solution and centrifuged at 12,718 g for 15 minutes and then recentrifuged at 14,700 g for 90 minutes. The supernatant is decanted and saved and filtered through sterile Nalgene 500 ml 0.45 μm filter. The sample is divided into four aliquots, i.e., each load is to be approximately 40 milliliters and phenylmethylsulfonyl chloride (PMSF) is added to a final concentration of 100 μm. Each sample load is designated D-1, D-2, D-3, and D-4, respectively. Prior to loading each sample onto the Reselute NK 2 immunoaffinity column (1.0×3.0 cm approximately 2.3 ml packed volume). The column is subjected to treatment with 10 cv of PBS, 10 cv of pH 2 citrate buffer then reequilibrated with 10 cv PBS. All steps are monitored by UV absorbance 280 nm detection at an AUF=0.10.

Run No. 1: Approximately 90 ml ($1.3 \times 10^8$ units of alpha interferon) of sample D-1, was loaded onto the column at a flow rate of approximately 30 ml per hour and any unbound material (designated U-1) was collected as a bulk fraction. The column was washed with phosphate buffer and a baseline reequilibration performed with phosphate buffer solution containing 0.1% (w/v) human serum albumin. Interferon was eluted with a pH 2 citrate buffer containing 0.1% (w/v) human serum albumin (HSA) at a flow rate of 20 ml per hour.

Run No. 2: Approximately 90 ml ($1.3 \times 10^8$ units of alpha interferon) of sample D-2 was loaded onto the column at a flow rate of approximately 30 ml per hour and the unbound material (designated U-2) was collected as bulk fraction. The column was washed with a phosphate buffer solution and a baseline reequilibration performed with phosphate buffer solution containing 0.5% (w/v) HSA. Interferon was eluted from the column with pH 2 citrate buffer containing 0.5% (w/v) HSA at a flow rate of 20 ml per hour.

Run No. 3: Approximately 90 ml ($1.3 \times 10^8$ units of alpha interferon) of sample D-3 was loaded onto the column at a flow rate of approximately 30 ml per hour and the unbound material (designated U-3) was collected as a bulk fraction. The column was washed with a phosphate buffer solution and a baseline reequilibration performed with phosphate buffer solution containing 0.1% (w/v) gelatin. Interferon was eluted with a pH 2 citrate buffer containing 0.1% (w/v) gelatin at a flow rate of 20 ml per hour.

Run No. 4: Approximately 90 ml ($1.3 \times 10^8$ units of alpha interferon) of sample D-4 was loaded onto the column at a flow rate of approximately 30 ml per hour and the unbound material (designated U-4) was collected as a bulk fraction. The column was washed with phosphate buffer solution and a baseline reequilibration performed with phosphate buffer solution containing 0.5% (w/v) gelatin. Interferon was eluted with a pH 2 citrate buffer containing 0.5% (w/v) gelatin of a flow rate of 30 ml per hour. The 0.5% (w/v) gelatin did not remain freely soluble at temperatures of about 2°-8° C. The column was repacked with warmed PBS 0.5% gelatin and maintained in a temperature range of 43° C. to 55° C. The pH 2 citrate 0.5% (w/v) gelatin buffer was maintained in the same temperature range.

Thus, Run No. 1 (sample D-1) is eluted with a buffer containing 0.1% (w/v) human serum albumin, Run No. 2 eluted interferon with a buffer containing 0.5% (w/v) human serum albumin, Run No. 3 eluted interferon with a buffer containing 0.1% (w/v) gelatin, and Run No. 4 eluted interferon with a buffer containing 0.5% (w/v) gelatin.

The specific activity of Run No. 1 (R1Fr6) was approximately $6.29 \times 10^7$ and the specific activity of Run No. 2 (R2Fr6) was approximately $9.4 \times 10^6$, thus indicating that a 5 fold increase in the concentration of albumin in the solution buffer lowers the specific activity of the final interferon product 6.6 fold following immunoaffinity chromatography.

The specific activity of Run No. 3 (R3Fr6) was $3.18 \times 10^8$ units per milligram and specific activity of Run No. 4 (R4Fr5) was approximately $5.25 \times 10^7$ units per milligram thus indicating that a 5 fold increase in the concentration of gelatin in the elution buffer results in a 6 fold lower specific activity of the end product.

The use of higher concentrations of human serum albumin or gelatin in the pH 2 eluting buffers during runs 2 and 4 caused significant decreases in the specific activity of the interferon compared to the specific activity of interferon eluted from column runs 1 and 3.

Although the illustrative embodiments of the present invention have been described herein with reference to the above-specification, it is to be understood that the invention is not limited to those precise embodiments, and that various changes in modifications may be effected therein by one skilled in the art without departing from the scope or spirit of the invention.

What is claimed is:

1. A method for controlling the resulting specific activity of a human leukocyte interferon-alpha composition during purification thereof, comprising providing an incubation medium of human leukocyte interferon-alpha, adding an effective amount of a controller protein selected from the group consisting of albumin and gelatin to a buffer eluent to form an protein buffer eluent composition, and contacting the protein buffer eluent composition with the interferon-alpha medium prior to the final step in the purification of the interferon-alpha to form an interferon-alpha and controller protein medium, purifying the interferon-alpha and controller protein medium by immunoaffinity chromatography, and collecting the interferon-alpha and protein product at the desired specific activity.

2. The method of claim 1, wherein the controller protein is albumin.

3. A method for controlling the resulting specific activity of a human leukocyte interferon-alpha composition during purification there, comprising providing an incubation medium of human leukocyte interferon-alpha, adding an effective amount of human serum albumin, to a buffer eluent composition, and contacting the human serum albumin and buffer eluent composition with the interferon-alpha medium prior to the final step in the purification of the interferon-alpha to form an interferon-alpha and human serum albumin medium, purifying the interferon-alpha and human serum albumin medium by immunoaffinity chromatography, and collecting the interferon-alpha and the human serum albumin product at the desired specific activity.

* * * * *